US010416080B1

(12) United States Patent
Pereira Masiero et al.

(10) Patent No.: US 10,416,080 B1
(45) Date of Patent: Sep. 17, 2019

(54) DEVICE FOR SENSING PHOTOLUMINESCENT MATERIALS IN SEAWATER

(71) Applicant: OURO NEGRO TECNOLOGIAS EM EQUIPAMENTOS INDUSTRIAIS S/A, Rio de Janeiro (BR)

(72) Inventors: Leone Pereira Masiero, Volta Redonda (BR); Luiz Carlos Guedes Valente, Rio de Janeiro (BR)

(73) Assignee: OURO NEGRO TECNOLOGIAS EM EQUIPAMENTOS INDUSTRIAIS S/A, Rio de Janeiro - RJ (BR)

( * ) Notice: Subject to any disclaimer, the term of this patent is extended or adjusted under 35 U.S.C. 154(b) by 0 days.

(21) Appl. No.: 15/884,714

(22) Filed: Jan. 31, 2018

(51) Int. Cl.
*G01N 21/64* (2006.01)
*G01N 33/18* (2006.01)
*G01N 21/65* (2006.01)

(52) U.S. Cl.
CPC .......... *G01N 21/64* (2013.01); *G01N 21/65* (2013.01); *G01N 33/1833* (2013.01); *G01N 2201/068* (2013.01)

(58) Field of Classification Search
CPC .... G01N 21/64; G01N 21/65; G01N 33/1833; G01N 2201/068
See application file for complete search history.

(56) References Cited

U.S. PATENT DOCUMENTS

| 3,666,945 A * | 5/1972 | Frungel ............... G01N 21/64 250/365 |
| 4,178,512 A * | 12/1979 | Frungel ............... G01N 21/645 250/253 |
| 4,282,487 A | 8/1981 | Warren et al. |
| 4,446,370 A * | 5/1984 | Gergely ............... G01N 21/645 250/301 |
| 5,481,904 A * | 1/1996 | Fleck, Sr. ............... G01N 1/12 340/605 |
| 5,604,582 A * | 2/1997 | Rhoads ............... G01J 3/2823 250/458.1 |
| 8,017,928 B2 * | 9/2011 | McStay ............... G01N 21/8507 250/458.1 |
| 8,030,934 B2 | 10/2011 | Barsukov et al. |
| 8,124,931 B2 * | 2/2012 | Andrews ............... G01N 21/35 250/301 |
| 8,445,841 B2 | 5/2013 | Szobota et al. |
| 8,916,816 B2 | 12/2014 | Tjhang et al. |
| 9,052,276 B2 | 6/2015 | Matsiev et al. |

(Continued)

*Primary Examiner* — Christine S. Kim
(74) *Attorney, Agent, or Firm* — Malin Haley DiMaggio & Bowen, P.A.

(57) ABSTRACT

The present invention refers to a device for sensing photoluminescent materials, said device comprising at least a source of light configured to generate a beam of light that is transmitted to the outside of said device and hits a photoluminescent material; a photon counting detector configured to receive a response light generated by the illumination of photoluminescent material with said beam of light and convert it into an electrical signal; a signal processing electronic system configured to process said generated electrical signal; and a signal transmission means configured to transmit the signals generated by the said signal processing electronic system towards the outside of the said device.

9 Claims, 3 Drawing Sheets

(56) References Cited

U.S. PATENT DOCUMENTS

| | | | |
|---|---|---|---|
| 9,146,225 B2 | 9/2015 | Pottorf et al. | |
| 9,217,317 B2 | 12/2015 | Backes | |
| 9,222,892 B2 | 12/2015 | Tunheim et al. | |
| 9,244,051 B2 | 1/2016 | Josse et al. | |
| 9,274,055 B2* | 3/2016 | Tedetti | G01N 21/645 |
| 9,298,193 B2 | 3/2016 | Susko | |
| 2005/0122225 A1* | 6/2005 | Kram | G01M 3/38 |
| | | | 340/605 |
| 2009/0014325 A1 | 1/2009 | Jones et al. | |
| 2012/0038362 A1 | 2/2012 | Kjerstad et al. | |
| 2012/0059585 A1 | 3/2012 | Kjerstad et al. | |
| 2014/0256055 A1 | 9/2014 | Pottorf et al. | |
| 2014/0284465 A1 | 9/2014 | Pottorf et al. | |
| 2014/0288853 A1 | 9/2014 | Dreyfus et al. | |
| 2014/0303895 A1 | 10/2014 | Dreyfus et al. | |
| 2015/0192488 A1 | 7/2015 | Xu et al. | |
| 2015/0241296 A1 | 8/2015 | Agbakwuru et al. | |
| 2015/0285060 A1 | 10/2015 | Albinsson et al. | |

* cited by examiner

DEVICE FOR SENSING PHOTOLUMINESCENT MATERIALS IN SEAWATER

FIELD OF THE INVENTION

The present invention belongs to the field of sensing devices for materials exhibiting photoluminescence in a specific optical frequency, particularly employing a method of light exciting the material and further detection of the emitted or scattered light using a photon counting detector. The emitted and further analyzed light may result from photoluminescence or from Raman scattering or from the combination of both techniques.

BACKGROUND INFORMATION

Nowadays, most widely used methods for hydrocarbon oil detection are based on methods using capacitive properties, photoluminescence with conventional detection (without photon counting), subsea images, satellite-processed images, conventional spectroscopy, module or derivative of the electromagnetic field and acoustic sensing.

A few of these well-known methods are the object of the U.S. patent documents U.S. Pat. Nos. 4,282,487, 9,217,317, 9,146,225, 9,052,276, 8,916,816, 8,445,841, 9,244,051, 9,222,892, 9,298,193, 8,030,934, US 20150285060, US 20150241296, US 20150192488, US20140303895, US 20140288853, US 20140284465, US 20140256055, US 20120059585, US 20120038362 and US 20090014325.

State-of-the-art technique for use in hydrocarbon oil detection resulting from oil spills are discussed in the paper by M. N. Jha, J. Levy et al "Advances in Remote Sensing for Oil Spill Disaster Management: State-of-the-Art Sensors Technology for Oil Spill Surveillance" Sensors. January, 2008, n° 8, pages 236-255.

The paper Oil Spill Detection by Satellite Remote Sensing by C. Brekke and A. H. S. Solberg, of March, 2005 pages 1-13 in "Remote Sensing of Environment" reports different automatic and manual approaches for using satellite sensors for oil spill detection.

One of the most commonly used techniques for hydrocarbon oil detection in the sea is by photoluminescence. This technique is being used for a long time for detecting oil spills on the sea surface and more recently, for detecting the presence of hydrocarbon oil in mixtures with seawater at great depths. However, the maximum distance between sensor and oil spills is very limited because of the low sensitivity of the photo detectors used and to the power limitation of the light sources.

Besides the reasons cited above, low detection sensitivities render prohibitive the use of optical fibers throughout long distances because of the high attenuation of these fibers in the visible spectrum wavelengths of petroleum oil fluorescence, that is, in the neighborhood of 500 nm.

One of the ways of identifying a molecule of a certain material is by Raman spectrometry, wherein a small fraction of the incident light on the material to be characterized is inelastically scattered at a frequency that differs from that of the incident light. Such variation in frequency, which occurs independently of the frequency of the emitted light, enables one to obtain information on the intrinsic characteristics of the molecule of the material to be analyzed. However, as the fraction of inelastically scattered light is very small, the detection of such light is extremely difficult.

Thus, the technique is still in need of a technical solution which could enable the efficient detection of photoluminescent particles (for example, petroleum oil) even when there is a significant distance between the detector and the particle.

OBJECTIVES OF THE INVENTION

One objective of the invention is to provide a device for sensing photoluminescent materials in seawater, the device having high detection sensitivity while at the same time allowing augmented distance between the sensor and the photoluminescent particle.

Another objective of the invention is to provide a device for sensing photoluminescent materials in seawater, such device allowing the use of optical fibers to convey photoluminescent light to detectors situated at a huge distance from the region of photoluminescence emission.

A further objective of the invention is to provide a device for sensing photoluminescent materials in seawater, the said device being useful for the detection of petroleum oil in offshore or subsea installations.

SUMMARY OF THE INVENTION

The present invention fulfills such and further objectives by means of a device for sensing photoluminescent materials in seawater, such device comprising: a) at least one source of light configured to generate a light beam which is transmitted towards the outside of the device and hits a photoluminescent material;

b) at least one photon counting detector configured to receive a response light generated by the illumination of the photoluminescent material with the said light beam and convert it into an electrical signal;

c) at least one signal processing electronic system configured to process said electrical signal; and d) at least one signal transmission means configured to convey the signals generated by the signal processing electronic system towards the outside of the said device.

Preferably, the source of light comprises a light emitting device and a driver electronic circuit electrically connected to the said light emitting device.

According to a first mode of the invention, the device comprises a mechanical encapsulation which houses the source of light, the photon counting detector and the signal processing electronic system. In this mode, the mechanical encapsulation further houses an optical system configured to transmit and receive light between the internal and external sides of the device, an optical filter connected to the photo detector, and an optical multiplexer/demultiplexer.

The optical multiplexer/demultiplexer has a first, a second and a third terminals, the first terminal being connected to the source of light, the third terminal being connected to the optical filter, while the second terminal is connected to the optical system, so that the light generated by the source of light enters through the first terminal and exits through the second terminal, and that a response light signal enters through the second terminal and exits through the third terminal towards the optical filter.

Preferably, the signal transmission means is an umbilical cable connected to the mechanical encapsulation. The umbilical cable is also utilized as a source of energy supply.

According to a second mode of the invention, the device comprises:
a) a first mechanical encapsulation that houses the source of light and comprises a first light transmission optical system; and b) at least one second mechanical encapsulation that houses the signal processing electronic system, the photon counting detector, an optical filter connected to the said detector and a light reception optical system, so that the light generated by the source of light crosses the light transmission optical system to hit the photoluminescent material, and the response light is received by the light reception optical system and crosses the optical filter towards the photo detector.

In this mode, the signal transmission means is an umbilical cable connected to the first mechanical encapsulation and to the second mechanical encapsulation. Preferably, the umbilical cable is also utilized as a source of power.

According to a third mode of the invention, the sensing device comprises:
a) at least one peripheral module with a mechanical encapsulation to house a source of light, an optical system configured to transmit and receive light between the internal and external sides of the device, an optical filter, and an optical multiplexer/demultiplexer having first, second and third terminals, the first terminal being connected to the source of light, the third terminal being connected to the optical filter while the second terminal is connected to the optical system, so that the light generated by the source of light enters through the first terminal and exits through the second terminal, and that a response light signal enters through the second terminal and exits through the third terminal towards the optical filter, and
b) a central module with a mechanical encapsulation that houses an optical signal multiplexer, the photon counting detector, and the signal processing electronic system;
wherein the signal transmission means is an umbilical cable connected to the central module and to the peripheral module, the umbilical cable being provided with optical fibers for transmitting the response light of the optical filter towards the central module.

The response light can be, for example, a photoluminescence light, a Raman inelastic scattering light or an elastic scattering light.

Preferably, the photon counting detector is selected among an array of photon counting detectors, a photomultiplier, one or more avalanche photodiodes, an array of avalanche photodiodes, a superconductor bolometer or a detector of superconducting nanothreads.

BRIEF DESCRIPTION OF THE DRAWINGS

The present invention will be hereinafter described with more detail by reference to the attached Figures, where.

DETAILED DESCRIPTION OF THE INVENTION

Figure 1:
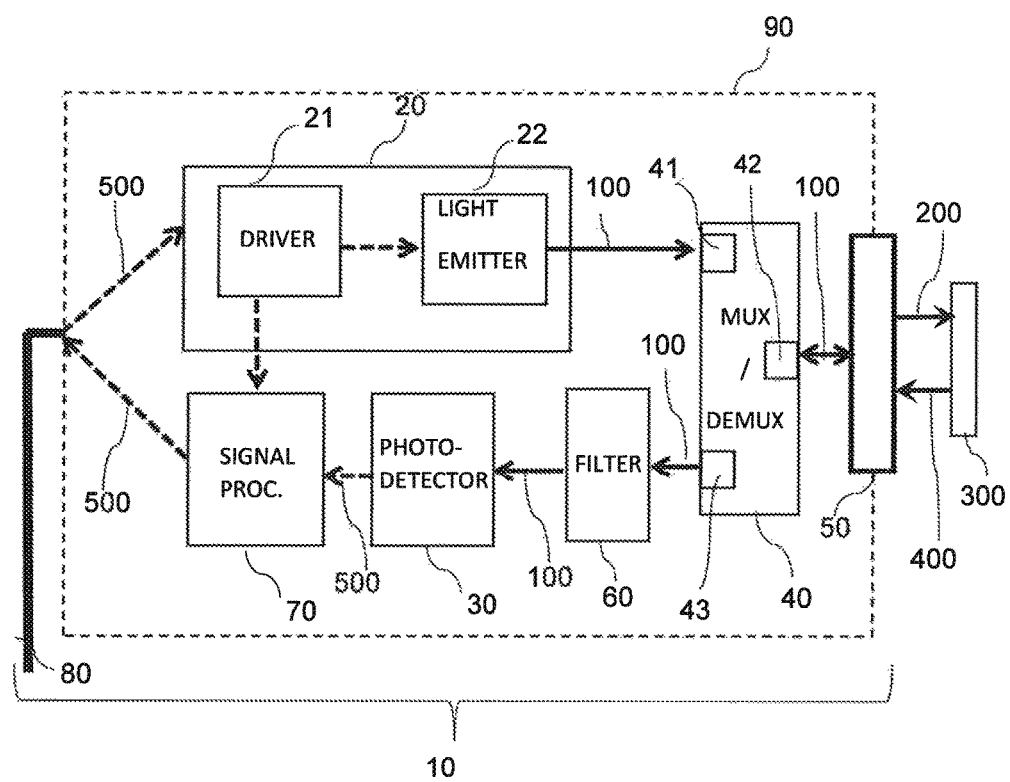
FIG. 1 is a schematic representation of the sensing device according to a first mode of the invention.

The present invention will be hereinafter described on the basis of Examples of three preferred modes of the sensing device according to the present invention.

The sensing device 10 according to the present invention comprises at least one source of light 20, at least one photon counting detector 30, at least one signal processing electronic system 70 and at least one signal transmission means 80.

The source of light 20 is utilized to generate an excitation collimated beam 200 that is emitted towards the external surface of device 10, where is located the photoluminescent element 300. Preferably, beam 200 is generated by an optical system 50. Thus, light generated by the source of light 20 propagates through a propagation medium 100 towards the said optical system 50, which converts same into the excitation collimated beam 200. Said beam 200 is emitted towards the external surface of device 10 where the photoluminescent element 300 is positioned.

Upon being illuminated by the excitation beam 200, the photoluminescent element 300 emits a response light 400. Said response light can be, for example, photoluminescence light, Raman inelastic scattering light or elastic scattering light.

Said light hits back on device 10 and hits on photon counting detector 30. The device 30 of the present invention can be any photo detector based on the photon counting principle. Preferably a silicon avalanche photodiode is used, but other devices such as photomultiplier tubes, superconducting bolometers and superconducting nanothread detectors are also within the scope of the invention.

The photon counting detector 30 converts the response light 400 into an electrical signal to be processed by the signal processing electronic system 70.

The obtained electrical signals are conveyed towards the outside of device 10, for example, with the aid of an umbilical cable 80. It should be stressed, however, that the transmission of electrical signals towards the outside of device 10 could be performed by any suitable means, for example, with the aid of other wire transmission means or wireless transmission means.

Preferably, umbilical cable 80 is in charge of additionally performing energy supply to all of the optoelectronic components of device 10. It should be stressed however that energy supply of device 10 can be performed by any other suitable means, such as for example, a battery.

Components of device 10 can be housed in a mechanical encapsulation 90. In this way, when the device is installed in a harsh environment, the components are housed in encapsulation 90 and have their energy supplied by umbilical cable 80. The same umbilical cable 80 is utilized for transmitting electrical signals generated by the signal processing electronic system 70.

FIG. 1 illustrates a first mode of the device of the present invention. In this mode, device 10 comprises a mechanical encapsulation 90 where are housed a source of light 20, a photon counting detector 30, an optical multiplexer/demultiplexer 40, an optical light transmission and reception system 50, an optical filter 60 and a signal processing electronic system 70, a transmission light medium 100 and electrical connections 500. An umbilical cable 80 is connected to encapsulation 90 for electrical signals transmission and for energy supply of device 10.

Preferably, the source of light 20 is made up of a driver electronic circuit 21 and a light emitting device 22. Both devices 21, 22 are interconnected by said electrical connection 500. Besides, a further electrical connection 500 is set up between the driver electronic circuit 21 and the signal processing system 70.

The energy supply of the said driver electronic circuit 21 is achieved by an electrical connection 500. Its goal is to generate electrical signals at its exit so as to inform the light emitting device 22 the temporal characteristics of the light to be emitted.

The light emitting device 22 is an optoelectronic component, such as a Laser, LED or lamp, able to generate light in the spectral ranges of interest (ultraviolet or visible) whenever electrically stimulated by the said driver electronic circuit 21. Besides, depending on the received electrical signal, the light emitting device 22 can emit light of different levels of optical power, different pulse emission rates and different pulse widths.

Propagating media 100, by which it is possible to propagate both light emitted by source of light 20 and light from the material in the external medium 400, can correspond to vacuum propagation, air propagation or by means of an optical fiber cable.

Light emitted by source of light 20 is propagated by propagating means 100 until it reaches terminal 41 of the optical multiplexer/demultiplexer 40.

Optical multiplexer/demultiplexer 40 element has three terminals 41, 42 and 43. Terminal 41 is connected to the source of light 20, terminal 43 to the optical filter 60, and terminal 42 to optical system 50, all by means of a propagating medium 100, which can correspond to air propagation or by means of an optical fiber cable. Its goal is to allow a light signal generated by the source of light 20 to enter through terminal 41 and exit through terminal 42, and a fluorescence light signal to enter through terminal 42 and exit through terminal 43.

There are several ways of implementing the optical multiplexer/demultiplexer 40 element. In case propagating media 100 are vacuum or air, a possible implementation would be a dichroic mirror, that reflects all the light in the optical frequency ranges of the source of light 20 and transmits all the light in the range of the optical frequency range of the light from the response light 400 generated by the photoluminescent material 300. Alternatively, in case propagating means 100 are optical fiber cables, a fibrated wave length multiplexer (WDM), an optical circulator or any other multiplexing/demultiplexing optical devices are useful for the purposes of the invention.

Terminal 42 of multiplexer/demultiplexer element 40 is optically connected via a propagating means 100 with an optical transmission and reception system 50.

The optical transmission and reception system 50 is in charge of providing an interface between the internal and external media to mechanical encapsulation 90. Such system enables the light generated by source of light 20 to be directed to the exterior of mechanical encapsulation 90 as an excitation beam 200, as well as enables fluorescence or Raman scattering light 400 originated from a photoluminescent element 300 to be captured towards the interior of said mechanical encapsulation 90.

Preferably, the optical transmission and reception system 50 comprises optical elements such as lenses, couplers, mirrors and diaphragms. The setup of the internal components of optical system 50 are responsible for parameters such as diameter and divergence of the excitation beam 200, as well as for the angular acceptance (numerical aperture) relative to the fluorescence or Raman scattering light 400.

In the presence of an element 300 hit by the excitation beam 200 a response light will be generated such as a photoluminescence and Raman scattering light 400 of optical frequency different from the optical frequency of the excitation beam 200. A portion of said light 400 will hit the optical transmission and reception system 50, with the result that the response light 400 is transmitted to the interior of the photoluminescence sensor device 10.

The photoluminescence and the inelastically scattered light 400 which hits the optical transmission and reception system 50 is then directed towards terminal 42 of optical multiplexer/demultiplexer 40 with the aid of propagating medium 100, to thereafter exit optical multiplexer/demultiplexer 40 through door 43 towards optical filter 60, after crossing propagating medium 100.

Optical filter 60 is any optical device transparent to the spectral range of the photoluminescent and inelastically scattered light 400 and at the same time opaque to all the remaining frequencies to which photo detector 30 is sensitive, mainly to the spectral range occupied by the light emitted by the source of light 20. That is, the optical spectrum of the light reaching photo detector 30 is confined to the limits determined by optical filter 60.

The possible implementations of optical filter 60 comprise different pass-band or low-pass filter configurations by utilizing suitable materials and/or thin film coatings, as well as Fabry-Pérot cavities or diffraction gratings.

The photoluminescence and/or the Raman scattering light filtered by the optical filter 60 is then directed towards photo detector 30 with the aid of a propagation medium 100. On its turn, photo detector 30 converts the detected light into an electrical signal, which is conveyed to the signal processing electronic system 70 by means of electrical connection 500.

The signal processing electronic system 70 formats and extracts relevant information from the analogical signals produced by photo detector 30 and converts them into digital signals, these being conveyed to umbilical cable 80 by means of electrical connection 500.

Preferably, the signal processing electronic system 70 comprises an electronic circuit able to correlate electrical signals received from electronic driver 21 and photo detector 30 to extract information such as propagation time of excitation light 200 up to the photoluminescent element 300, distance between photo detector 30 and photoluminescent element 300, decay rate of the photoluminescence or Raman scattering light 400 for estimating the concentration and kind of element 300, or any other information which could be extracted from the photon counting data and propagation times.

Umbilical cable 80 is in charge of transmitting electrical signals to the exterior or mechanical encapsulation 90, especially in cases where the photoluminescence sensor device 10 is in an environment hostile to other forms of transmission of electrical signals such as for example, in submarine environment. Besides, umbilical cable 80 is in charge of supplying all of the optoelectronic components within mechanical encapsulation 90.

Mechanical encapsulation 90 can have cylindrical, cubic, parallelepiped or any geometric shape able to support the elements composing the sensor. Encapsulation 90 can be made up of metal, polymers or any other material resistant to the high pressures to which the sensor will be exposed in the marine bed.

Figure 2:
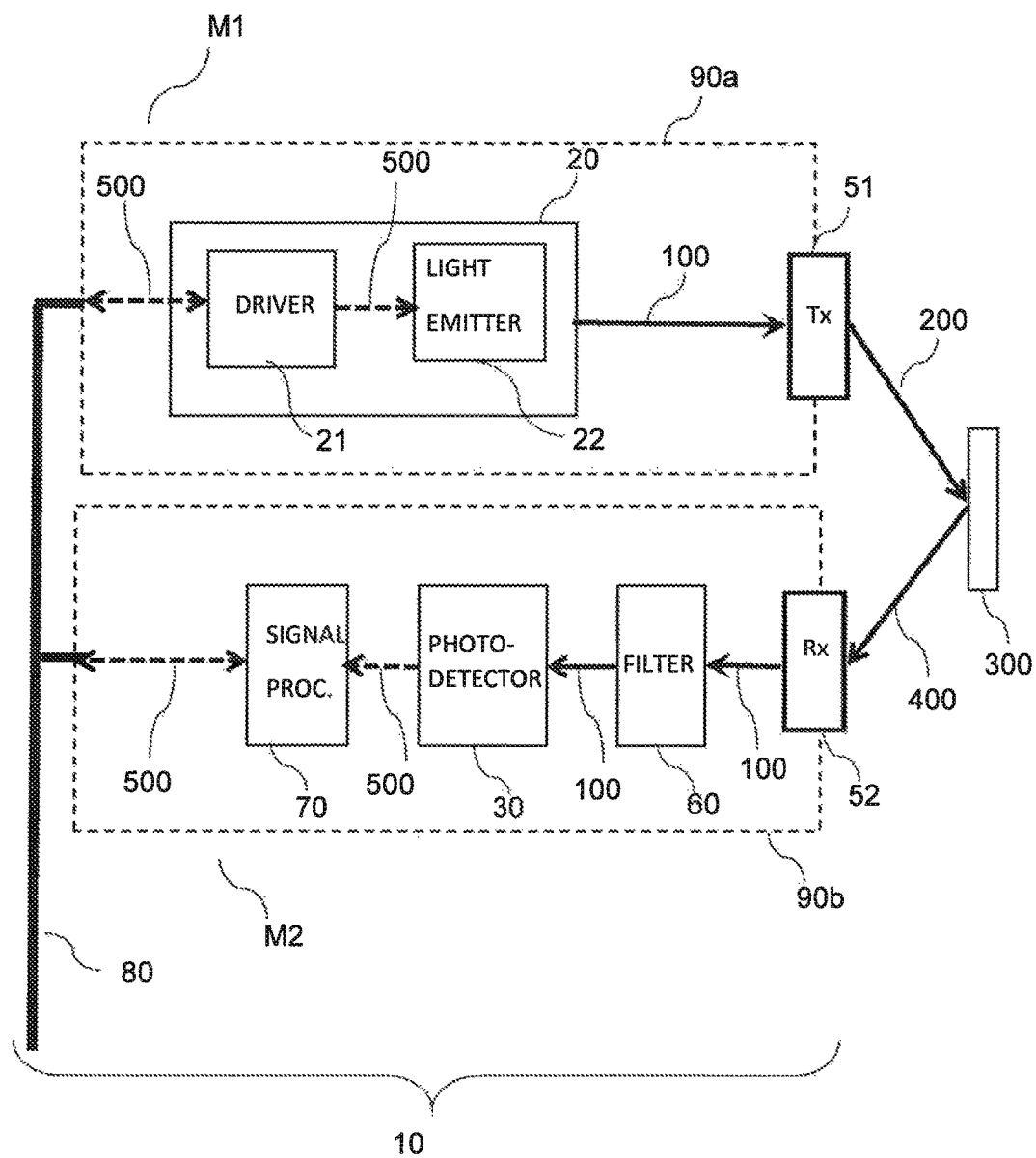
FIG. 2 is a schematic representation of the sensing device according to a second mode of the invention.

FIG. 2 illustrates a second mode of the device of the present invention.

According to this configuration, a sensor device 10 comprises at least two disjoint mechanical encapsulations 90a, 90b forming two distinct modules M1, M2. The first module M1 comprises a source of light 20, a light transmission optical system 51, an umbilical cable 80, a mechanical encapsulation 90, a light transmission medium 100 and electrical connections 500. The second module M2 has a photon counting detector 30, a light reception optical system 52, an optical filter 60, a signal processing electronic system 70, an umbilical cable 80, a mechanical encapsulation 90, a light transmission medium 100 and electrical connections 500. The interaction between sensor device 10 and element 300 is identical to that already described hereinbefore in the present specification for the first mode of the invention.

In this mode of the invention, the optical transmission and reception system 50 of the said first mode was replaced by two different optical systems, the optical transmission system 51 and the reception optical system 52, both identical to the optical transmission and reception system 50 already mentioned. For this reason, the optical multiplexer/demultiplexer 40 of the first mode is unnecessary.

The advantage of the second mode of the invention is the possibility of spatially adjusting the transmission and reception light modules at different positions. This is especially advantageous in the case the region of space to be measured is very well delimited and if there are previous evidences that the light 400 from material 300 is not emitted in isotropic form.

Besides, the mode of the invention with distinct modules enables a set up to be created where several photo detection modules M2 can be connected, via umbilical cable 80, with the light emission module M1.

Figure 3:
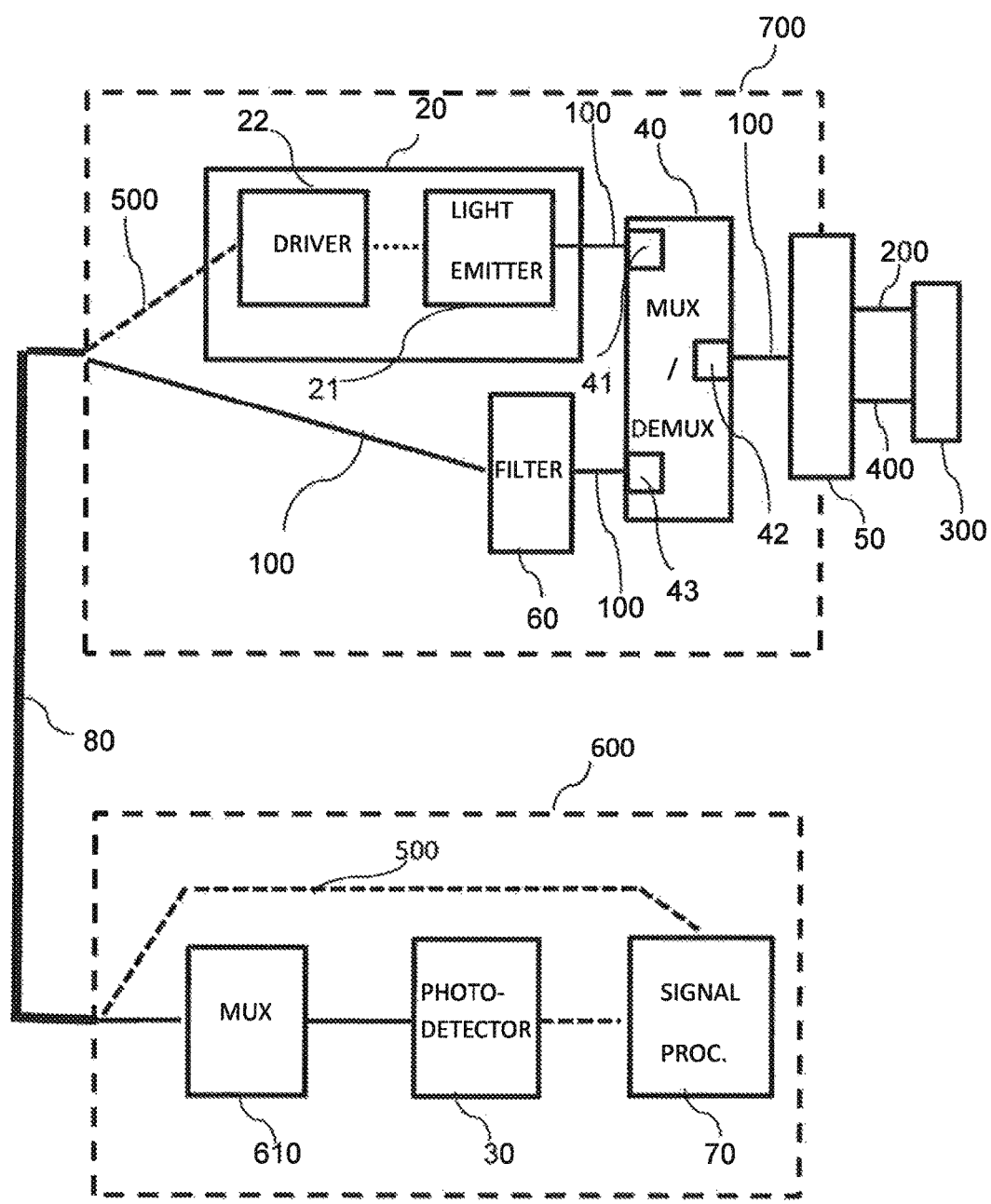
FIG. 3 is a schematic representation of the sensing device according to a third mode of the invention.

FIG. 3 illustrates a third mode of the device of the present invention.

In this mode, sensor device 10 comprises two or one central module 600 and one or more peripheral modules 700. Each peripheral module 700 comprises a source of light 20, an optical multiplexer/demultiplexer 40, an optical transmission and reception system 50, an optical filter 60, an umbilical cable 80, a mechanical encapsulation 90, a light transmission medium 100 and electrical connections 500.

Central module 600 has an optical signal multiplexer 610, a photon counting detector 30, a signal processing electronic system 70, an umbilical cable 80, a mechanical encapsulation 90, a light transmission medium 100 and electrical connections 500.

According to this mode, the interaction between the photoluminescence sensor device 10 and the photoluminescent element 300 is identical to that related to the said first mode of the invention.

This mode allows several peripheral modules 700 to be connected to a central module 600.

Thus, the optical signals multiplexer 610 of the central module can be implemented by an optical key actuated by electromechanical, electro-optical, acoustic-optic or non-linear optics effect, so that it is possible to connect one single photo detector or a set of photo detectors 30 to a set of optical fibers which in turn are connected to umbilical cables of any of the peripheral modules 700.

The advantage of this mode of the invention is to make possible that one single detector can be used to perform the detection of photoluminescence light signals originating from several distinct geographical points, which may or may not be far from each other. For example, photoluminescence measurements at great ocean depths could be performed while the photo detector is at the surface.

Thus, the equipment according to the third mode of the present invention could be configured for application in fluorescence sensing in the subsea environment, such as for example, for the detection of hydrocarbon oil in the sea bottom. In this application, the central module 600 would be placed in a central position which would not be necessarily located below sea level, while one or more peripheral modules would be submerged in the sites where it is desired to detect the hydrocarbon oil presence.

Thus, having described three preferred modes of the present invention, it should be understood by the experts that the scope of the present invention comprehends further possible variations of the described inventive concept, said variations being limited only by the content of the appended claims, being included therein all and every equivalent modes.

The invention claimed is:

1. A device for sensing photoluminescent materials in seawater comprising:
   at least one source of light configured to generate a beam of light that is transmitted to the outside of said device and hits a photoluminescent material;
   at least one photon counting photo detector configured to receive a response light generated by the illumination of said photoluminescent material by the beam of light and convert said response light into an electrical signal;
   at least one signal processing electronic system configured to process said generated electrical signal;
   at least one signal transmission means configured to transmit the signals generated by the said signal processing electronic system towards the outside of said device;
   at least a peripheral module provided with a mechanical encapsulation to house the source of light, an optical system configured to transmit and receive light between the internal and external surfaces of device; an optical filter and an optical multiplexer/demultiplexer having first, second, and third terminals, the first said terminal being connected to said source of light, the third terminal being connected to said optical filter, while the second terminal is connected to said optical system, so that the light generated by the source of light enters through the first terminal and exits through said second terminal, and that a response light signal enters through the said second terminal and exits through the said third terminal towards the optical filter; and
   a central module having a mechanical encapsulation to house an optical signal multiplexer, the photon counting detector and the signal processing electronic system,
   wherein the signal transmission means is an umbilical cable connected to the central module and to the peripheral module, the umbilical cable having optical fibers to transmit the response light of the optical filter to the central module.

2. The device according to claim 1, wherein:
   the response light is selected among any of photoluminescence light, Raman inelastic scattering light or elastic scattering light.

3. The device according to claim 1, wherein:
   the photon counting detector is selected among an array of photon counting detectors, a photomultiplier, one or more avalanche photodiodes, an array of avalanche photodiodes, a superconductor bolometer or a superconductor nanothread detector.

4. The device according to claim 1, said source of light comprising a light emitting device and a driver electronic circuit electrically connected to said light emission device.

5. The device according to claim 1, including a mechanical encapsulation to house the source of light, the photon counting photo detector and the signal processing electronic system, the mechanical encapsulation housing including an optical system configured to transmit light between the internal and external surfaces of device.

6. The device according to claim 1, wherein said mechanical encapsulation further houses an optical filter connected to said photo detector, and an optical multiplexer/demultiplexer having a first, a second, and a third terminal, the first said terminal being connected to said source of light, the third terminal being connected to said optical filter, while the second terminal is connected to said optical system, so that the light generated by the source of light enters through the first terminal and exits through said second terminal, and that a response light signal enters through the said second terminal and exits through the said third terminal towards the optical filter.

7. The device according to claim 1, wherein said at least one signal transmission means is an umbilical cable connected to mechanical encapsulation, and wherein said umbilical cable is also utilized as a source of energy supply.

8. The device according to claim 1, further comprising:
 a first mechanical encapsulation to house the source of light and which comprises a first optical light transmission system;
 at least a second mechanical encapsulation which houses the signal processing electronic system, the photon counting detector, an optical filter connected to the photo detector and an optical light reception system;
 such that the light generated by the source of light crosses the optical light transmission system to hit the photoluminescent material and the response light is received by the optical light reception system and crosses the optical filter owards the photo detector.

9. The device according to claim 1, wherein said signal transmission means is an umbilical cable connected to said first mechanical encapsulation and to said second mechanical encapsulation, and wherein said umbilical cable is also utilized as a source of energy supply.

* * * * *